United States Patent [19]

Buchanan et al.

[11] 4,122,273
[45] Oct. 24, 1978

[54] BICYCLO[2.2.1]-HEPTANE-2,3-DI-ENDO-CARBOXYLIC ACID IMIDE ESTERS

[75] Inventors: Ronald Leslie Buchanan, Fayetteville; John Theodore Woolever, Chittenango, both of N.Y.; Alex Michael Jelenevsky, Nashville, N.C.

[73] Assignee: Bristol-Myers Company, New York, N.Y.

[21] Appl. No.: 877,521

[22] Filed: Feb. 13, 1978

Related U.S. Application Data

[62] Division of Ser. No. 715,951, Aug. 19, 1976.

[51] Int. Cl.² ........................................... C07D 403/12
[52] U.S. Cl. ................... 544/355; 544/116; 544/128; 544/142; 260/332.2 R
[58] Field of Search ............... 544/355, 116, 128, 142

[56] References Cited

U.S. PATENT DOCUMENTS

| | | | |
|---|---|---|---|
| 3,850,921 | 11/1974 | Matuo | 544/372 |
| 3,850,922 | 11/1974 | Matuo | 544/372 |
| 3,936,449 | 2/1976 | Matuo et al. | 544/372 |
| 3,980,667 | 9/1976 | Partyka et al. | 544/372 |
| 3,980,668 | 9/1976 | Buchanan et al. | 544/372 |
| 4,018,767 | 4/1977 | Buyniski et al. | 544/372 |

Primary Examiner—Nicholas S. Rizzo
Assistant Examiner—David E. Wheeler
Attorney, Agent, or Firm—David M. Morse

[57] ABSTRACT

A series of 5-endo-(quinoxaline-carbonyloxy)-N[amino-(lower)alkyl]bicyclo[2.2.1]-heptane-2,3-di-endo-carboxylic acid imides has been found to possess excellent prophylactic and therapeutic activity as anti-arrhythmic agents.

16 Claims, No Drawings

BICYCLO [2.2.1]-HEPTANE-2,3-DI-ENDO-CARBOXYLIC ACID IMIDE ESTERS

CROSS-REFERENCE TO RELATED APPLICATION

This application is a division of our prior, co-pending application Ser. No. 715,951 filed August 19, 1976.

BACKGROUND OF THE INVENTION

This invention relates to a novel series of 5-endo(-quinoline-carbonyloxy)-, (benzothiophene-carbonyloxy)- and (quinoxaline-carbonyloxy)-N-[amino(lower)alkyl]bicyclo[2.2.1]-heptane-2,3-di-endo-carboxylic acid imides possessing anti-arrhythmic and/or anti-fibrillatory activity.

DESCRIPTION OF THE PRIOR ART (A.) British Pat. No. 1,042,840 describes compounds having the formula

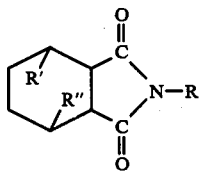

in which each of R' and R" represent hydrogen, or together an alkylene group having 1 or 2 carbon atoms, and R represents an alkyl group having 6 to 18, preferably 8 to 12 carbon atoms in a straight chain as having particularly advantageous properties as functional fluids.

(B.) U. S. Pat. No. 3,393,999 describes the compounds having the formula

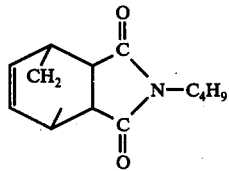

as being an effective insecticide.

(C.) U.S. Pat. No. 2,424,220 describes the compound having the formula

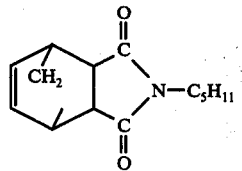

as being an effective insecticide.

(D.) U.S. Pat. No. 2,462,835 describes the compound having the formula

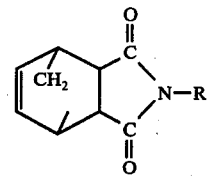

in which R is alkyl, alkene, aryl, substituted aryl, alkynyl, etc. as insecticides.

(E.) Culberson and Wilder, Jr., J. Org. Chem., 25, pp. 1358–62 (1960) report the preparation of compounds having the formula

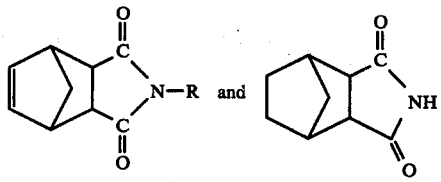

in which R is $CH_3$, $C_6H_{13}$ or hydrogen.

(F.) Rice, Reide and Grogan, J. Org. Chem., 19, pp. 884–893 (1954) report the preparation of compounds of the formula

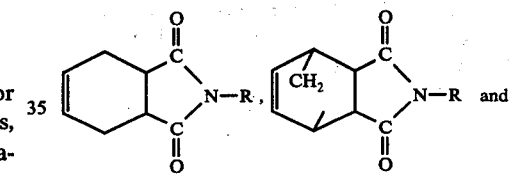

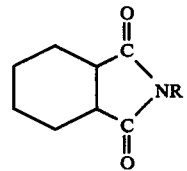

in which R is alkyl and their subsequent reduction with lithium aluminum hydride.

(G.) Worral, J. Am. Chem. Soc., 82, pp. 5707–5711 (1960) report the preparation of compounds having the formula

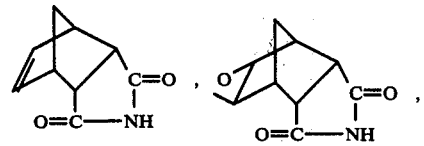

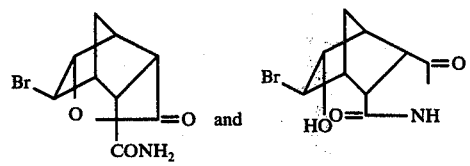

(H.) German Auslegeschrift No. 1,179,205 reports the preparation of compounds having the formula

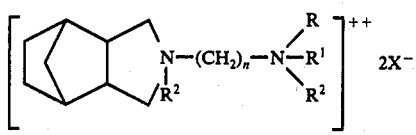

in which the bicyclo[2.2.2]octane ring system is saturated or unsaturated and/or substituted, R and $R^1$ are alkyl or alkenyl groups of 1 to 5 carbon atoms, or when combined with the nitrogen a heterocycle ring. $R^2$ is a (lower)alkyl group, n is a number of 2 to 5 and X a halogen anion. The quaternary compounds are described as having therapeutic properties in the treatment of cardiovascular disease, specifically high blood pressure.

(I.) U.S. Pat. No. 3,850,922 discloses and claims the compounds having the formula

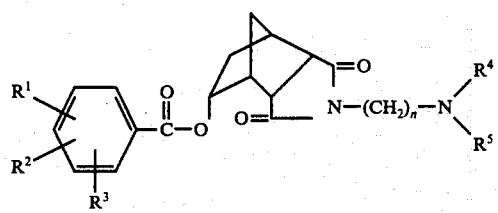

wherein $R^1$, $R^2$ or $R^3$ is H, Cl, Br, F, (lower)alkyl, nitro, OH or (lower)alkoxy, n is an integer of 2 to 4 inclusive and $R^4$ or $R^5$ is H, (lower)alkyl or when taken together with the nitrogen a radical of the formula

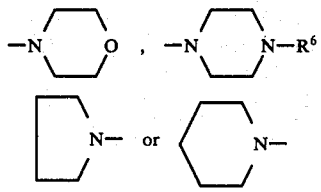

in which $R^6$ is (lower)alkyl; or a pharmaceutically acceptable acid addition salt thereof as antiarrhythmic agents.

(J.) U.S. Pat. No. 3,850,921 discloses and claims the compounds having the formula

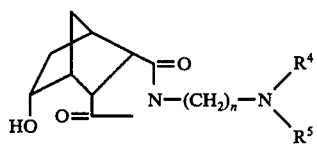

wherein n is an integer of 2 to 4 inclusive and $R^4$ and $R^5$ are H, (lower)alkyl or when taken together with the nitrogen a radical of the formula

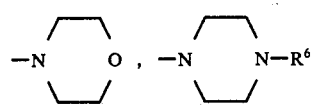

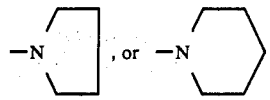

in which $R^6$ is (lower)alkyl; or an acid addition salt thereof as intermediates in the preparation of the antiarrhythmia compounds found in U.S. Pat. No. 3,850,922 supra.

(K.) U.S. Pat. No. 3,936,449 discloses the antiarrhythmic compounds having the formula

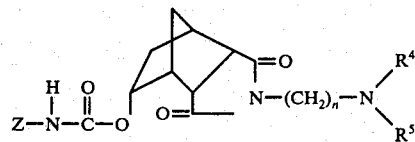

wherein Z is 3 or 4-pyridyl, (lower)alkyl, cyclohexyl, cyclopentyl, cycloheptyl, 1-adamantyl, cyclobutyl, cyclopropyl or a radical of the formula

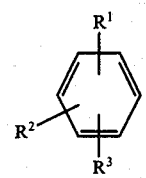

in which $R^1$, $R^2$ and $R^3$ are alike or different and each is H, Cl, Br, F, (lower) alkyl, nitro, Oh or (lower)alkoxy, n is an integer of 2 to 4 inclusive and $R^4$ and $R^5$ is H, (lower)alkyl, or, when taken together with the nitrogen, a radical of the formula

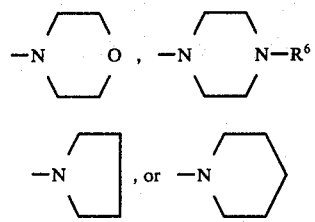

wherein $R^6$ is (lower)alkyl, and the pharmaceutically acceptable acid addition salts thereof.

L.) Belgian Pat. No. 833,385 discloses and claims the anti-arrhythmic compounds of the formula

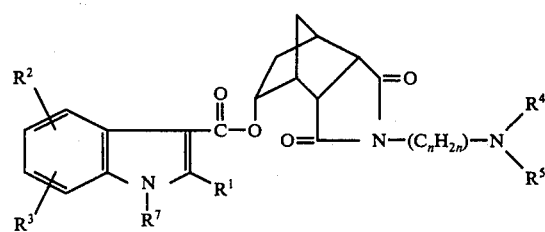

wherein $R^7$ is hydrogen or methyl, $R^1$ is chloro, bromo, fluoro, hydrogen or (lower)alkyl and $R^2$ and $R^3$ are alike or different and each is H, Cl, Br, F, (lower)alkyl, nitro, $CF_3$, OH or (lower)alkoxy, n is an integer of 2 to 4 inclusive and $R^4$ and $R^5$ are alike or different and each is H, (lower)alkyl or when taken together with the nitrogen a radical of the formula

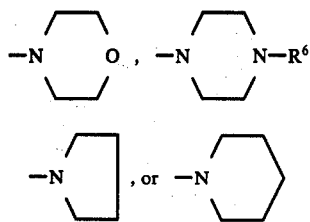

in which $R^6$ is (lower)alkyl; or pharmaceutically acceptable acid addition salts thereof.

SUMMARY OF THE INVENTION

Compounds having the formula

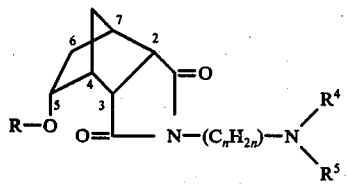   I wherein R is a radical of the formula

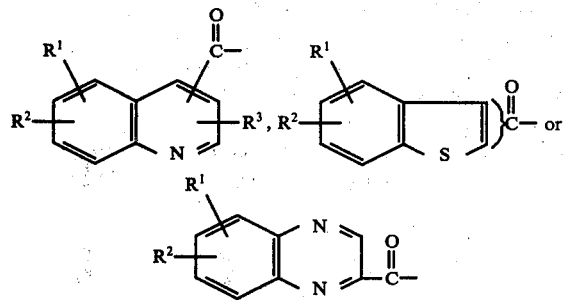

in which $R^1$ and $R^2$ are alike or different and are each hydrogen, chloro, bromo, fluoro, (lower)alkyl, nitro, trifluoromethyl, hydroxy or (lower)alkoxy, $R^3$ is hydrogen, chloro, bromo, fluoro, (lower)alkyl, hydroxy or (lower)alkoxy, n is an integer of 2 to 4 inclusive and $R^4$ and $R^5$ are alike or different and each is hydrogen, (lower)alkyl or, when taken together with the nitrogen, a radical of the formula

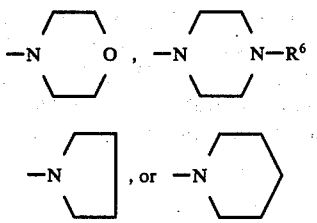

in which $R^6$ is (lower)alkyl, and pharmaceutically acceptable acid addition salts thereof are anti-arrhythmic agents.

Cardiac arrhythmia, a phenomenon commonly associated with coronary heart disease or myocardial infarction, is an affliction not uncommon in humans, especially the elderly. The mechanism of cardiac arrhythmia is suspected to be caused by an abnormal "focus" in the ventricle of the heart which sends out (fires) nerve signals more rapidly than required for the normal beating of the heart. Uncontrolled arrhythmia can lead to fibrillation which results in death.

It has now been discovered that the compounds of formula I are useful therapeutic or prophylactic agents in the suppression of the abnormal ectopic beat.

Compound I can theoretically exist in several isomeric forms, namely:

A. endo-heterocyclic-carbonyloxy: endo-substituted imide;

B. exo-heterocyclic-carbonyloxy: exo-substituted imide;

C. endo-heterocyclic-carbonyloxy: exo-substituted imide; and

D. exo-heterocyclic-carbonyloxy: endo-substituted imide.

Furthermore, each of these isomers has two optical isomers: levorotatory and dextrorotatory.

The distinction between the isomers is determined by the relative position of the constituent bonds at positions 2, 3 and 5 of the bicyclo ring system.

When these bonds, i.e., the constituent bonds at positions 2, 3 and 5 are on the same side as the $C_7$ bridge, we have the exo-exo isomer. When these bonds, i.e., the constituent bonds at positions 2, 3 and 5, are on the opposite side of the $C_7$ bridge or, alternatively, within the cage formed by carbon atoms 2, 3, 5 and 6, then we have the endo-endo isomer. When the constituent bond at position 5 is on the same side as the $C_7$ bridge and the constituent bonds 2 and 3 are on the opposite side of the $C_7$ bridge, we have the endoexo isomer. Illustrative of the exo-exo isomer is the compound having the formula

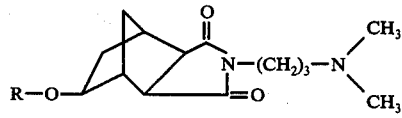

Illustrative of endo-endo is the compound of formula I.

The only isomers claimed in this invention are the endo-endo isomers as represented by compound I and the dextro- and levorotatory isomers thereof. The endo-endo isomers are inherently exclusively produced by the synthesis described herein.

The optical isomers of I can be separated and isolated by fractional crystallization of the diastereoisomeric salts formed, for instance, with (+) or (−)-tartaric acid or D-(+)camphor sulfonic acid (see general procedure in Belgian Pat. No. 833,385).

Alternatively, and preferably, the optical isomers of compound I can be prepared by resolving starting material compound III by the fractional crystallization of the diastereoisomeric salts formed, for instance, with (+) or (−) tartaric or D-(+)camphorsulfonic acid, followed by esterification to produce compound I.

For the purpose of this disclosure, the term "(lower)alkyl" is defined as an alkyl radical containing 1 to 6 carbon atoms. The alkyl radical can be branched or straight chained, e.g., n-propyl, isopropyl, etc. The representation $-(C_nH_{2n})-$ in which n is 2 to 4 is meant to include all variations of the radical, e.g., —CH$_2$—CH$_2$—CH$_2$—,

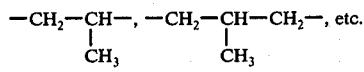

The term "(lower)alkoxy" is an alkoxy radical containing 1 to 6 carbon atoms. The term "pharmaceutically acceptable acid addition salt" is defined to include all those inorganic and organic acid salts of the compounds of the instant invention, which salts are commonly used to produce nontoxic salts of medicinal agents containing amine functions. Illustrative examples would be those salts formed by mixing the compounds of formula I with hydrochloric, sulfuric, nitric, phosphoric, phosphorous, hydrobromic, maleic, malic, ascorbic, citric or tartaric, pamoic, lauric, stearic, palmitic, oleic, myristic, laurylsulfonic, naphthalenesulfonic, linoleic or linolenic acid, and the like.

A preferred embodiment of the present invention is the compound having the formula

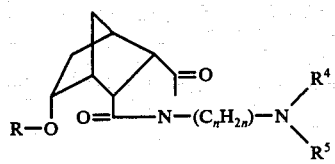

wherein R is a radical of the formula

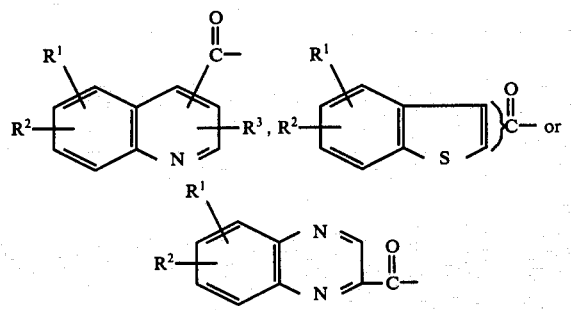

in which R$^1$ and R$^2$ are alike or different and are each hydrogen, chloro, bromo, fluoro, (lower)alkyl, nitro, trifluoromethyl, hydroxy or (lower)alkoxy, R$^3$ is hydrogen, chloro, bromo, fluoro, (lower)alkyl, hydroxy or (lower)alkoxy, n is an integer of 2 to 4 inclusive and R$^4$ and R$^5$ are alike or different and each is hydrogen, (lower)alkyl or, when taken together with the nitrogen, a radical of the formula

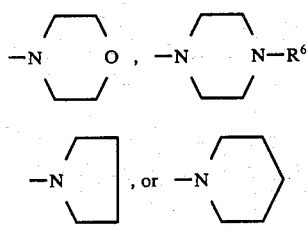

in which R$^6$ is (lower)alkyl; or a pharmaceutically acceptable acid addition salt thereof.

A more preferred embodiment of the present invention is the compound having the formula

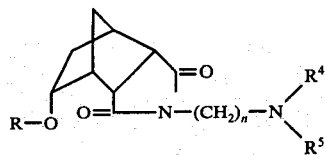

wherein R is a radical of the formula

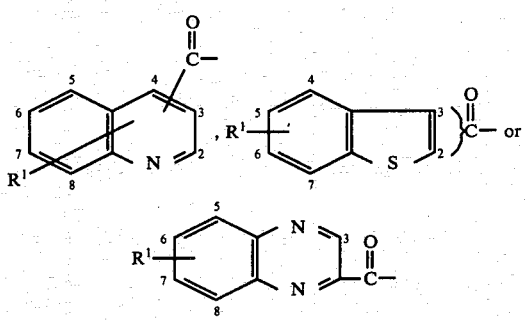

in which R$^1$ is hydrogen, chloro, bromo, fluoro, (lower)alkyl, nitro, trifluoromethyl, hydroxy or (lower)alkoxy with the proviso that the quinoline ring may not be substituted at positions 2, 3 or 4 by nitro or trifluoromethyl, n is an integer of 2 to 4 inclusive and R$^4$ and R$^5$ are alike or different and are each hydrogen, (lower)alkyl or, when taken together with the nitrogen, a radical of the formula

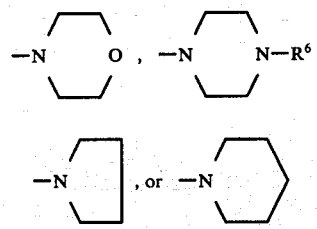

in which R$^6$ is (lower)alkyl; or a pharmaceutically acceptable acid addition salt thereof. Especially preferred compounds of the above formula are those where (a) n is an integer of 2 to 4 inclusive and R$_4$ and R$^5$ are alike or different and each is hydrogen or (lower)alkyl; (b) n is an integer of 2 to 4 inclusive and R$^4$ and R$^5$ are alike or different and each is hydrogen, methyl, ethyl or isopropyl; and (c) n is 3 and R$^4$ and R$^5$ are each methyl.

A most preferred embodiment of the present invention is the compound having the formula

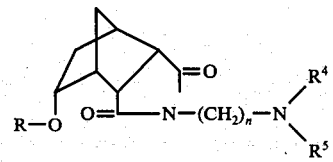

wherein R is a radical of the formula

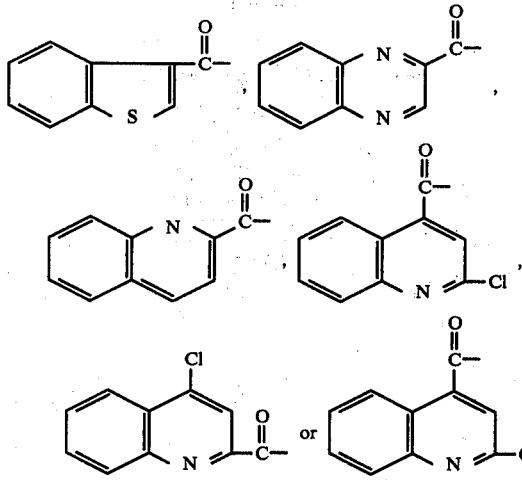

n is an integer of 2 to 4 inclusive and $R^4$ and $R^5$ are alike or different and are each hydrogen, (lower)alkyl or, when taken together with the nitrogen, a radical of the formula

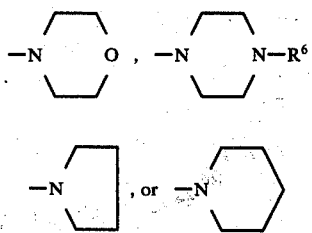

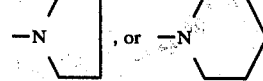

in which $R^6$ is (lower)alkyl; or a pharmaceutically acceptable acid addition salt thereof. Especially preferred compounds of the above formula are those where (a) n is an integer of 2 to 4 inclusive and $R^4$ and $R^5$ are alike or different and each is hydrogen or (lower)alkyl; (b) n is an integer of 2 to 4 inclusive and $R^4$ and $R^5$ are alike or different and each is hydrogen, methyl, ethyl or isopropyl; and (c) n is 3 and $R^4$ and $R^5$ are each methyl.

The most preferred compounds of the present invention are:

(a) the compound of the formula

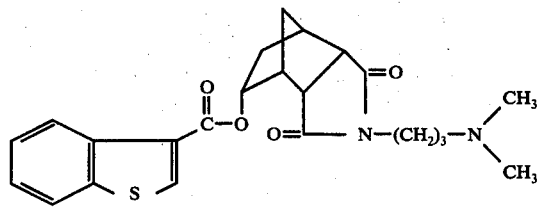

or a pharmaceutically acceptable acid addition salt thereof, most particularly the hydrochloride salt thereof;

(b) the compound of the formula

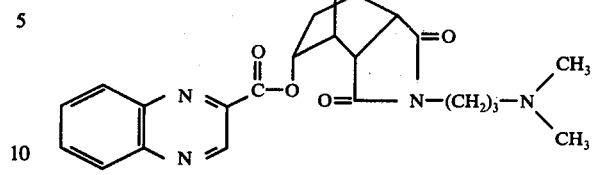

or a pharmaceutically acceptable acid addition salt thereof, most particularly the hydrochloride salt thereof;

(c) the compound of the formula

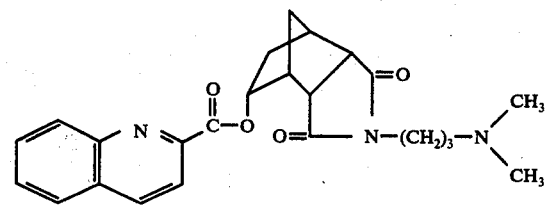

or a pharmaceutically acceptable acid addition salt thereof, most particularly the hydrochloride salt thereof;

(d) the compound of the formula

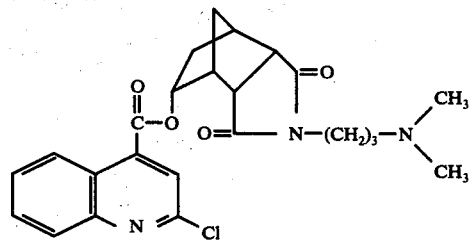

or a pharmaceutically acceptable acid addition salt thereof, most particularly the hydrochloride salt thereof;

(e) the compound of the formula

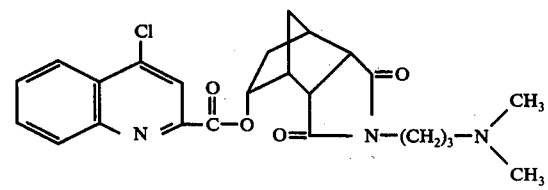

or a pharmaceutically acceptable acid addition salt thereof, most particularly the hydrochloride salt thereof; and (f) the compound of the formula

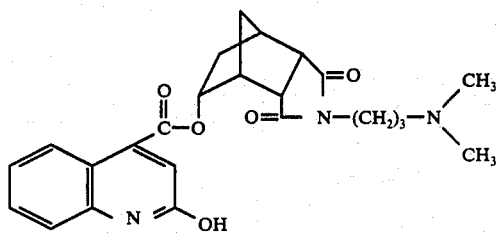

or a pharmaceutically acceptable acid addition salt thereof, most particularly the hydrochloride salt thereof.

The compounds and salts of formula I and the various preferred embodiments described above can exist in the form of a racemic mixture levorotatory and dextrorotatory optical isomers or in the form of the essentially pure levorotatory (−) isomers or dextrorotatory (+) isomers. Both the racemic and resolved forms of the compounds and salts are included within the scope of the present invention.

The compounds of formula I may be prepared by acylating one mole of an alcohol of the formula

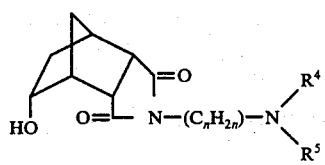

III wherein n is an integer of 2 to 4 inclusive, $R^4$ and $R^5$ are alike or different and each is hydrogen, (lower)alkyl or, when taken together with the nitrogen, a radical of the formula

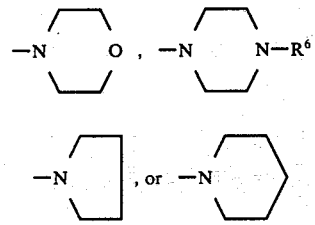

in which $R^6$ is (lower)alkyl with at least one mole of an acid halide of the formula

IV wherein R' is a radical of the formula

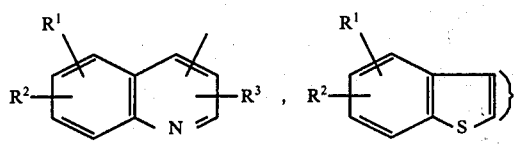

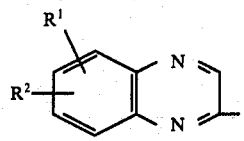

in which $R^1$ and $R^2$ are alike or different and each is hydrogen, chlor, bromo, fluoro, (lower)alkyl, nitro, trifluoromethyl, hydroxy or (lower)alkoxy, $R^3$ is hydrogen, chloro, bromo, fluoro, (lower)alkyl, hydroxy or (lower)alkoxy and X is chloro, bromo, or iodo, but preferably chloro, or its chemical equivalent as an acylating agent, in an inert organic solvent and at a temperature in the range of about 0° C. to 100° C.

Preparation of the alcohol starting materials of formula III is disclosed in Belgian Pat. No. 833,385 and in U.S. Pat. No. 3,850,921.

Examples of suitable inert organic solvents for use in the above process include aprotic organic solvents such as benzene, toluene, xylene, pyridine, methylene chloride, chloroform, acetonitrile or dioxane, or mixtures thereof.

The acylation may be conducted over a wide temperature range, e.g. 0° C, to about 100° C., and is conveniently carried out at the reflux temperature of the solvent system employed.

For the purpose of this invention, the term "chemical equivalent as an acylating agent" is meant to include all those agents commonly known in the art to be useful for the esterification of alcohols, for example, acid anhydrides and mixed acid anhydrides. The preferred acylating agents for preparing most of the compounds of formula I are the acid halides, most preferably the acid chlorides. To prepare the compounds of formula I, however, where $R^1$, $R^2$ or $R^3$ are hydroxy, it is preferred to use an imidazolide acylating agent formed by reaction of the desired carboxylic acid starting material with N,N'-carbonyl-diimidazole. Use of this procedure avoids side reactions during acylation and results in greatly improved yields of the desired hydroxy-substituted esters. An alternative preferred procedure for preparing hydroxy-substituted compounds comprises blocking the hydroxy functional group(s) of the starting carboxylic acid by a conventional blocking group, e.g. a benzyl group, converting the so-protected carboxylic acid to a carboxylic acid halide, e.g. acid chloride, esterifying the alcohol of formula III with the acid halide and removing the hydroxy-protecting group from the product ester, e.g. by catalytic hydrogenation to remove a benzyl group, to give the desired hydroxy-substituted product.

To prepare compounds of formula I where $R^4$ and $R^5$ are each hydrogen, i.e. the primary amine compounds, the preferred procedure involves acylation of the acid halide or chemical equivalent with the desired alcohol of the formula

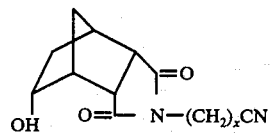

where x is an integer of 1 to 3 to produce a nitrile ester intermediate and then reduction of the nitrile group of said intermediate, e.g. by catalytic hydrogenation over a Pd/C catalyst, to give the primary amine end-product.

A preferred procedure for preparing compounds of formula I in which $R^4$ is hydrogen and $R^5$ is (lower)alkyl (or vice versa) comprises acylation with the desired carboxylic acid halide or chemical equivalent of an alcohol starting material of the formula

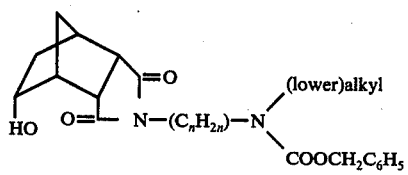

followed by hydrogenolysis of the so-produced intermediate to give the desired secondary amine ester.

The compounds of formula I may be prepared in the free base form or in the form of a pharmaceutically acceptable acid addition salt thereof, e.g. by treatment of the free base compound in a suitable solvent with a pharmaceutically acceptable acid. Alternatively, the acid addition salts of formula I may be converted to the corresponding free base compounds by neutralization, e.g. with $Na_2CO_3$.

The compounds of the present invention were tested in dogs for anti-arrhythmic activity. Anesthetized dogs were used for the production of ouabain-induced ventricular arrhytmias. The arrhythmia consisted of a nodal or ventricular tachycardia. The procedure used to establish the arrhythmia as well as the criteria employed to determine anti-arrhythmic activity generally was that employed by Lucchesi, et al.[1].

[1]. Lucchesi, B. L. and H. F. Hardman: The influence of dichloroisoproterenol (DCI) and related compounds upon ouabain and acetylstrophanthidin induced cardiac arrhythmias. J. Pharmacol. Exp Therap., 132:372 (1961)

Anti-arrhythmic activity of the compounds of Examples 1-5 and 7 was determined by rapid intravenous injection and compared to lidocaine and procainamide, two commercial anti-arrhythmic agents. The $ED_{100}$(mg./kg.) values for these compounds are shown below.

| Compound of Example | *$ED_{100}$(mg./kg.) |
| --- | --- |
| 1 (BL-4726 A) | ~3.0 |
| 2 (BL-4769 A) | ~1.0 |
| 3 (BL-4781 A) | ~1.0 |
| 4 (BL-4825 A) | ~0.3 |
| 5 (BL-4826 A) | ~1.0 |
| 7 (BL-4945 A) | ~1-3 |
| Procainamide | >10 |
| Lidocaine | 6.4 |

*Dose required for a reversion of arrhythmias of at least 30 minutes duration upon rapid iv infusion in anesthetized dogs.

The compounds of formula I are useful in the treatment of cardiac arrhythmia in mammals, including man, as prophylactic or therapeutic agents in doses in the range of 0.25 mg. to 3.0 mg./kg. up to 3 to 4 times a day. They may be administered either orally or parenterally. Additionally, the compound of Example 7, i.e. 5-endo-(2-hydroxyquinoline-4-carbonyloxy)-N-(3-dimethylaminopropyl)-bicyclo-[2.2.1]heptane-2,3-di-endo carboxylic acid imide hydrochloride (and its free base and other salts) exhibits hypotensive activity in mammals when administered parenterally in doses of from about 1 to 5 mg./kg. up to 3 to 4 times a day.

In preparing the anti-arrhythmic compounds of the present invention, other compounds were synthesized having the general formula

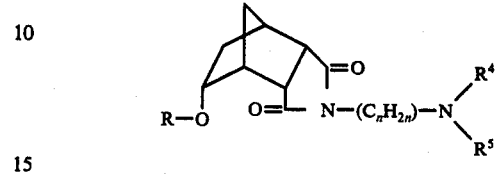

where R is a bicyclic heteroaromatic radical. Quabain arrhythmia ($ED_{100}$) data in anesthetized dogs is shown below for three such compunds:

| COMPOUND | $ED_{100}$ (mg./kg.) |
| --- | --- |
| BL-4721 A; R = [indene-carbonyl structure] | Toxic at 1.0 |
| BL-4676 A; R = [isochromandione structure] | Toxic at 3.0 |
| BL-4761 A; R = [benzofuran-2-carbonyl structure] | Toxic at 1.0 |

The above data clearly shows the importance of the heterocyclic "R" group in the compounds of general formula I and the unobvious nature of the present invention in discovering those particular heterocyclic rings which result in pharmaceutically useful anti-arrhythmic agents.

The following examples are given in illustration of but not in limitation of, the present invention. All temperatures are in degrees Centigrade. The starting material alcohols, i.e. the 5-endo-hydroxy-N-[amino(lower-)alkyl]-bicyclo[2.2.1]heptane-2,3-di-endo-carboxylic acid imides, and the end products mentioned in the examples are racemic (±) mixtures of the dextrorotatory and levorotatory optical isomers unless otherwise indicated.

EXAMPLE 1

5-endo-(2-Quinaldoyloxy)-N-(3-dimethylaminopropyl)-bicyclo-[2.2.1]heptane-2,3-di-endo carboxylic acid imide hydrochloride (BL-4726 A)

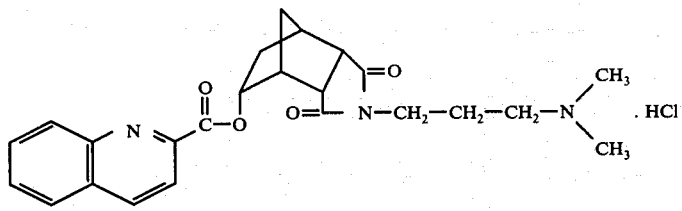

A mixture of quinaldic acid (6.92 g., 0.04 mole) and thionyl chloride (6 ml.) in dry $CH_2Cl_2$ (75 ml.) was refluxed for 2 hours, giving a bright red solution. Removal of excess reagent and solvent under reduced pressure afforded the crude acid chloride. This acid chloride (7.24 g., 0.04 mole) was dissolved in dry $CH_2Cl_2$ (50 ml.) and 5-endo-hydroxy-N-(3-dimethylaminopropyl)-bicyclo[2.2.1]heptane-2,3-di-endo carboxylic acid imide (5.32 g., 0.02 mole) was added, followed by 20 ml. of dry pyridine. A deep violet color developed and the mixture was stirred at 23° for 72 hr. The reaction mixture was then diluted with $CH_2Cl_2$ (100 ml.) and 5% $Na_2CO_3$ solution (200 ml.). The layers were separated and the $CH_2Cl_2$ layer was washed with two additional 100 ml. portions of 5% $Na_2CO_3$. The organic layer was dried ($MgSO_4$) and stripped of solvent to give a dark oil. Extraction of the aqueous washes with two portions of ethyl acetate yielded a red solid after removal of solvent. The oil and solid were combined and treated with refluxing isopropyl alcohol. Cooling gave the free base of the title product as a light red solid (mp. 141°–142°). Treatment with $HCl_g$ in ethyl acetate gave the hydrochloride salt (2.86 g., 31.5%). Recrystallization from ethyl acetate-acetonitrile afforded an analytical sample of the title product (mp. 204°–205°).

Anal. Calc'd. for $C_{24}H_{27}N_3O_4 \cdot HCl$: C, 62.94; H, 6.16; N, 9.18; Cl, 7.74. Found: (corrected for 2.56% $H_2O$): C, 63.25; H, 6.02; N, 9.43; Cl, 7.95.

EXAMPLE 2

5-endo-(Benzothiophene-3-carbonyloxy)-N-(3-dimethylaminopropyl)-bicyclo[2.2.1]heptane-2,3-di-endo carboxylic acid (BL-4769 A)

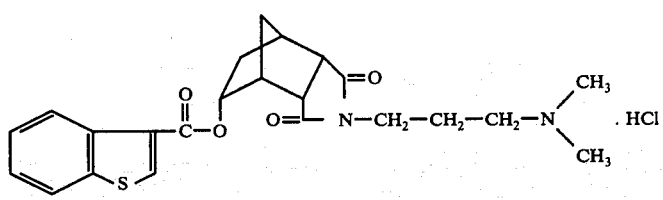

Benzothiophene-3-carboxylic acid was prepared from 3-acetyl benzothiophene (Bull. Soc. Chim. France, p. 1534, 1961) according to the method disclosed in U.K. Pat. No. 944,417. This acid (2.5 g., 0.014 mole) was converted to the acid chloride according to the procedure used in Example 1. The crude acid chloride (2.7 g., 0.014 mole) was then dissolved in dry $CH_2Cl_2$ (50 ml.). Dry pyridine (3 drops) and 5-endo-hydroxy-N-(3-dimethylaminopropyl)-bicyclo[2.2.1]heptane-2,3-di-endo carboxylic acid imide (2.7 g., 0.01 mole) were then added and the mixture was stirred at reflux for 70 hr. Solvent removal under reduced pressure, two recrystallizations of the resultant residue from ethanol, and treatment with boiling ethyl acetate afforded analytical material after drying under high vacuum over $P_2O_5$ (2.6 g., 52%, mp. 246°–250°).

Anal. Calc'd. for $C_{23}H_{26}N_2O_4S \cdot HCl$: C, 59.66; H, 5.88; N, 6.05; Cl, 7.66; S, 6.92. Found: (corrected for 0.86% $H_2O$): C, 59.20; H, 5.90; N, 5.90; Cl, 7.72; S, 6.82.

EXAMPLE 3

5-endo-(Quinoxaline-2-carbonyloxy)-N-(3-dimethylaminopropyl)-bicyclo[2.2.1]hetpane-2,3-di-endo carboxylic acid imide hydrochloride (BL-4781 A)

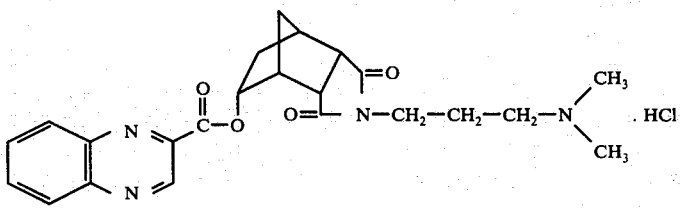

To a solution of 2-quinoxaloyl chloride (5.0 g., 0.026 mole) in dry $CH_2Cl_2$ (50 ml.) and pyridine (4 drops) was added 5-endo-hydroxy-N-(3-dimethylaminopropyl)-bicyclo[2.2.1]heptane-2,3-di-endo carboxylic acid imide (4.6 g., 0.0175 mole). The red colored mixture was stirred at reflux for 2 hours and the solvent was then removed under reduced pressure. The remaining dark red gum was treated with decolorizing charcoal in hot ethanol and then recrystallized from ethanol to give the pure title product as white crystals (3.15 g., 39%, mp. 238°-240°).

Anal. Calc'd. for $C_{23}H_{26}N_4O_4 \cdot HCl$: C, 60.18; H, 5.93; N, 12.21; Cl, 7.73. Found: (corrected for 1.1% $H_2O$): C, 60.30; H, 5.78; N, 12.09; Cl, 7.60.

EXAMPLE 4

5-endo-(2-Chloroquinoline-4-carbonyloxy)-N-(3-dimethylaminopropyl)-bicyclo[2.2.1]heptane-2,3-di-endo carboxylic acid imide hydrochloride (BL-4825 A)

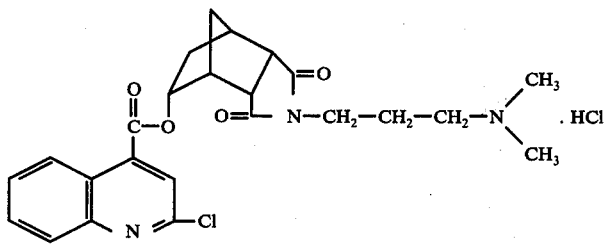

2-Hydroxycinchoninic acid (1.89 g., 0.001 mole) was suspended in dry $CH_2Cl_2$ (60 ml.) and thionyl chloride (3.0 ml.) was added, followed by 1 ml. of dry dimethylformamide. The mixture was stirred at reflux for 16 hr., giving a homogeneous yellow solution. Stripping of solvents and excess reagent gave the crude chloro acid chloride. The acid chloride (2.2 g.) and 5-endo-hydroxy-N-(3-dimethylaminopropyl)-bicyclo[2.2.1]-heptane-2,3-di-endo carboxylic acid imide (2.5 g., 0.0094 mole) were then dissolved in dry $CH_2Cl_2$ (50 ml.) and dry pyridine (1 ml.) and stirred at reflux for 2 hr. The dark red solution was then stripped of solvent and the residual gum was dissolved in 100% ethanol, treated with $HCl_g$ and stripped to dryness. Trituration of the semisolid residue with 1:1 ethyl acetate:absolute ethanol yielded a solid (1.487 g., 32%). Recrystallization from 100% ethanol-methanol gave an analytical sample of title product (mp. 273°-275° d.).

Anal. Calc'd. for $C_{24}H_{26}ClN_3O_4 \cdot HCl$: C, 58.54; H, 5.53; N, 8.53; Cl, 14.40. Found: C, 58.46; H, 5.76; N, 8.74; Cl, 14.09.

EXAMPLE 5

5-endo-(4-Chloroquinoline-2-carbonyloxy)-N-(3-dimethylaminopropyl)-bicyclo[2.2.1]heptane-2,3-di-endo carboxylic acid imide hydrochloride (BL-4826 A)

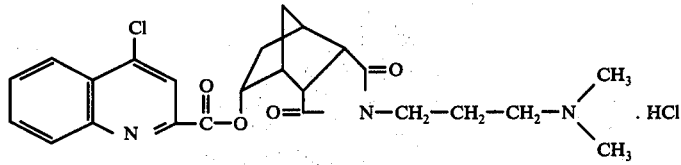

A mixture of 4-hydroxyquinoline-2-carboxylic acid (1.89 g., 0.001 mole) and thionyl chloride (3.0 ml.) in dry $CH_2Cl_2$ (50 ml.) containing 1 ml. of dry dimethylformamide was stirred at reflux for 3 hr., resulting in a clear yellow solution. Cooling deposited the chloro acid chloride as yellow crystals. After filtration, the acid chloride (0.687 g.) was mixed with 5-endo-hydroxy-N-(3-dimethylaminopropyl)-bicyclo[2.2.1]heptane-2,3-di-endo carboxylic acid imide (0.8 g., 0.003 mole) in dry $CH_2Cl_2$ (20 ml.) containing 0.5 ml. of dry pyridine. After stirring at 23° under an $N_2$ atmosphere for 18 hr., the red solution was stripped to dryness under reduced pressure. The resultant red gum was dissolved in 25 ml. of 100% ethanol from which the title product (0.872 g., 58.9%) separated upon standing at 23°. Recrystallization from 100% ethanol gave the pure material as colorless needles (mp. 172°-178°).

Anal. Calc'd. for $C_{24}H_{26}ClN_3O_4 \cdot HCl$: C, 58.54; H, 5.53; N, 8.53; Cl, 14.40. Found: (corrected for 4.54% $H_2O$): C, 58.34; H, 5.16; N, 8.38; Cl, 14.55.

EXAMPLE 6

5-endo-(4-Hydroxyquinoline-2-carbonyloxy)-N-(3-dimethylaminopropyl)-bicyclo[2.2.1]heptane-2,3-di-endo carboxylic acid imide dihydrochloride (BL-4937 A)

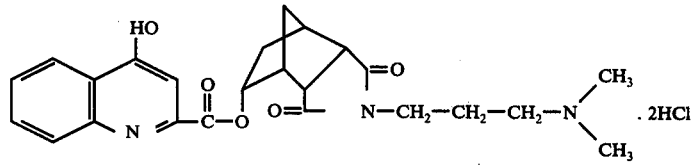

A mixture of 4-hydroxyquinoline-2-carboxylic acid (1.89 g., 10 mmole) and carbonyldiimidazole (3.24 g., 20 mmole) in dry tetrahydrofuran (70 ml.) was stirred at reflux for 16.5 hours under an atmosphere of dry nitrogen, forming a homogeneous solution of the intermediate imidazolide of the formula

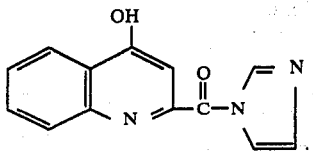

A solution of 5-endo-hydroxy-N-(3-dimethylaminopropyl)-bicyclo[2.2.1]heptane-2,3-di-endo carboxylic acid imide (2.66 g., 10 mmole) in 25 ml. of hot tetrahydrofuran was then added to the reaction mixture over 1-2 minutes. The mixture was then stirred at reflux under dry $N_2$ for an additional 22.5 hr., whereupon the solvent was removed under reduced pressure and the resultant oil dissolved in hot 1:1 ethyl acetate:diethyl ether. The cooled solution deposited the free base of the title product as a solid (0.925 g., mp. 200°–208° d.). The dihydrochloride (0.82 g., 17.3%) was prepared in the usual manner (HClg) in 5:1 ethanol:methanol and recrystallization from ethanol:ethyl acetate afforded the title product (mp. 260°–265° d.).

Anal. Calc'd. for $C_{24}H_{27}N_3O_5 \cdot 2HCl$: C, 56.48; H, 5.73; N, 8.23; Cl, 13.89. Found: C, 56.40; H, 5.83; N, 8.19;

EXAMPLE 7

5-endo-(2-Hydroxyquinoline-4-carbonyloxy)-N-(3-dimethylaminopropyl)-bicyclo-[2.2.1]heptane-2,3-di-endo carboxylic acid imide hydrochloride (BL-4945 A)

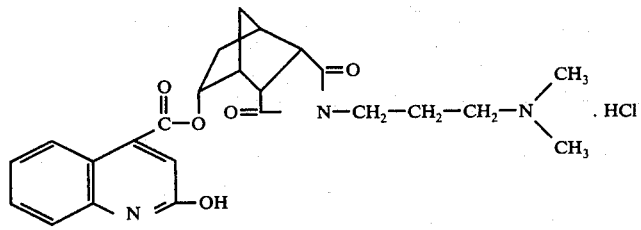

A mixture of 2-hydroxycinchoninic acid (0.946 g. 5 mmole) and carbonyldiimidazole (1.62 g., 10 mmole) in dry tetrahydrofuran (50 ml.) was stirred in an atmosphere of dry $N_2$ at reflux for 2.75 hr. and then at 20° for 19.5 hr. The solid precipitate of the imidazolide intermediate was filtered, washed with diethyl ether and air dried (0.84 g., mp. 213°–217° d.). This intermediate (0.83 g., 3.47 mmole) was then suspended in dry tetrachloroethane (75 ml.) along with 5-endo-hydroxy-N-(3-dimethylaminopropyl)-bicyclo[2.2.1]heptane-2,3-di-endo carboxylic acid imide (0.665 g., 2.5 mmole) and heated with stirring to 60°. Hydrogen chloride was then bubbled into the solution causing a temperature rise to approximately 72° lasting for about 5 minutes and a small quantity of yellow solid precipitated initially and then redissolved. Heating at 85° with HCl addition was continued for 40 minutes, followed by heating at 105°–110° for 16 hrs. The solvent was then removed under reduced pressure and the gummy residue was partitioned between ethyl acetate and 5% $NaHCO_3$ solution. The organic layer was washed with water and brine and then dried over anhydrous $MgSO_4$. Solvent removal and trituration of the resultant semisolid gum with 3:1 diethyl ether:ethyl acetate gave the free base of the title product as a pale yellow solid (0.505 g., 46.2%). The hydrochloride salt was formed in the usual manner (addition of HCl gas) in 1:1 ethanol:methanol and recrystallized from 3:1 ethanol:methanol (mp. 290°–292° d.).

Anal. Cacl'd. for $C_{24}H_{27}N_3O_5 \cdot HCl$: C, 60.82; H, 5.95; N, 8.87. Found: (corrected for 1.86% $H_2O$): C, 60.86; H, 5.83; N, 8.68.

In addition to anti-arrhythmic activity, BL-4945 A also was found to provide sustained blood pressure lowering at 5 mg./kg. when administered by bolus injection to anesthetized dogs having ouabain-induced ventricular arrhythmias. No undesirable side effects were seen on the electrocardiogram at this dosage.

EXAMPLE 8

Substitution in the general procedures of Examples 1–7 for the carboxylic acid or carboxylic acid halide used therein of an equimolar amount of the acylating acids listed below (converted to the acid chloride in the procedure of Example 3) produces the indicated products.

PRODUCT

| ACID | M= |
|---|---|
| quinoline-3-carboxylic acid | quinoline-3-carbonyloxy |
| quinoline-4-carboxylic acid | quinoline-4-carbonyloxy |
| quinoline-5-carboxylic acid | quinoline-5-carbonyloxy |
| quinoline-6-carboxylic acid | quinoline-6-carbonyloxy |
| quinoline-7-carboxylic acid | quinoline-7-carbonyloxy |
| quinoline-8-carboxylic acid | quinoline-8-carbonyloxy |
| *4-hydroxyquinoline-2-carboxylic acid | 4-hydroxyquinoline-2-carbonyloxy |
| 4-methylquinoline-2-carboxylic acid | 4-methylquinoline-2-carbonyloxy |
| 4-ethoxyquinoline-2-carboxylic acid | 4-ethoxyquinoline-2-carbonyloxy |

-continued

PRODUCT

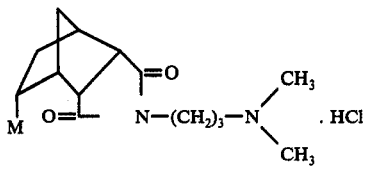

| ACID | M= |
|---|---|
| 6-methylquinoline-2-carboxylic acid | 6-methylquinoline-2-carbonyloxy |
| 6-nitroquinoline-2-carboxylic acid | 6-nitroquinoline-2-carbonyloxy |
| *8-hydroxyquinoline-2-carboxylic acid | 8-hydroxyquinoline-2-carbonyloxy |
| *4,6-dihydroxyquinoline-2-carboxylic acid | 4,6-dihydroxyquinoline-2-carbonyloxy |
| *4,8-dihydroxyquinoline-2-carboxylic acid | 4,8-dihydroxyquinoline-2-carbonyloxy |
| 5-methylquinoline-2-carboxylic acid | 5-methylquinoline-2-carbonyloxy |
| 6-methoxyquinoline-2-carboxylic acid | 6-methoxyquinoline-2-carbonyloxy |
| 7-nitroquinoline-2-carboxylic acid | 7-nitroquinoline-2-carbonyloxy |
| 8-nitroquinoline-2-carboxylic acid | 8-nitroquinoline-2-carbonyloxy |
| 6-chloroquinoline-2-carboxylic acid | 6-chloroquinoline-2-carbonyloxy |
| 4,7-dichloroquinoline-2-carboxylic acid | 4,7-dichloroquinoline-2-carbonyloxy |
| 2-chloroquinoline-3-carboxylic acid | 2-chloroquinoline-3-carbonyloxy |
| *2-hydroxyquinoline-3-carboxylic acid | 2-hydroxyquinoline-3-carbonyloxy |
| 2-methylquinoline-3-carboxylic acid | 2-methylquinoline-3-carbonyloxy |
| 2-methoxyquinoline-3-carboxylic acid | 2-methoxyquinoline-3-carbonyloxy |
| 4-chloroquinoline-3-carboxylic acid | 4-chloroquinoline-3-carbonyloxy |
| *4-hydroxyquinoline-3-carboxylic acid | 4-hydroxyquinoline-3-carbonyloxy |
| 4-methylquinoline-3-carboxylic acid | 4-methylquinoline-3-carbonyloxy |
| 6-methoxyquinoline-3-carboxylic acid | 6-methoxyquinoline-3-carbonyloxy |
| 2-ethylquinoline-4-carboxylic acid | 2-ethylquinoline-4-carbonyloxy |
| 2-methoxyquinoline-4-carboxylic acid | 2-methoxyquinoline-4-carbonyloxy |
| 3-ethylquinoline-4-carboxylic acid | 3-ethylquinoline-4-carbonyloxy |
| 7-chloroquinoline-4-carboxylic acid | 7-chloroquinoline-4-carbonyloxy |
| *6-hydroxyquinoline-4-carboxylic acid | 6-hydroxyquinoline-4-carbonyloxy |
| 7-bromoquinoline-4-carboxylic acid | 7-bromoquinoline-4-carbonyloxy |
| 7-fluoroquinoline-4-carboxylic acid | 7-fluoroquinoline-4-carbonyloxy |
| 5-methoxyquinoline-4-carboxylic acid | 5-methoxyquinoline-4-carbonyloxy |
| 6-methoxyquinoline-4-carboxylic acid | 6-methoxyquinoline-4-carbonyloxy |
| 6,8-dimethoxyquinoline-4-carboxylic acid | 6,8-dimethoxyquinoline-4-carbonyloxy |
| 5-nitroquinoline-4-carboxylic acid | 5-nitroquinoline-carbonyloxy |
| benzothiophene-2-carboxylic acid | benzothiophene-2-carbonyloxy |
| 5-chlorobenzothiophene-3-carboxylic acid | 5-chlorobenzothiophene-3-carbonyloxy |
| 5-nitrobenzothiophene-3-carboxylic acid | 5-nitrobenzothiophene-3-carbonyloxy |
| 5-methylbenzothiophene-2-carboxylic acid | 5-methylbenzothiophene-2-carbonyloxy |
| 5-methoxybenzothiophene-3-carboxylic acid | 5-methoxybenzothiophene-3-carbonyloxy |
| 5,6-dimethoxybenzothiophene-2-carboxylic acid | 5,6-dimethoxybenzothiophene-2-carbonyloxy |
| 4-bromobenzothiophene-2-carboxylic acid | 4-bromobenzothiophene-2-carbonyloxy |
| 6-chloroquinoxaline-2-carboxylic acid | 6-chloroquinoxaline-2-carbonyloxy |
| 7-chloroquinoxaline-2-carboxylic acid | 7-chloroquinoxaline-2-carbonyloxy |
| 6,7-dimethoxyquinoxaline-2-carboxylic acid | 6,7-dimethoxyquinoxaline-2-carbonyloxy |
| 6-methylquinoxaline-2-carboxylic acid | 6-methylquinoxaline-2-carbonyloxy |

-continued

PRODUCT

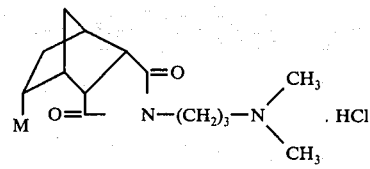 . HCl

| ACID | M= |
|---|---|
| 7-methylquinoxaline-2-carboxylic acid | 7-methylquinoxaline-2-carbonyloxy |
| 6-nitroquinoxaline-2-carboxylic acid | 6-nitroquinoxaline-2-carbonyloxy |
| 7-nitroquinoxaline-2-carboxylic acid | 7-nitroquinoxaline-2-carbonyloxy |

*Procedure of Example 6 or 7 used.

EXAMPLE 9

5-endo-(2-Chloroquinoline-4-carbonyloxy)-N-(2-dimethylaminoethyl)-bicyclo[2.2.1]heptane-2,3-di-endo carboxylic acid imide hydrochloride (Compound of formula I where R=2-chloroquinoline-4-carbonyl, n=2, $R^4$ and $R^5$=CH$_3$)

Substitution in the procedure of Example 4 for the 5-endo-hydroxy-N-(3-dimethylaminopropyl)-bicyclo[2.2.1]heptane-2,3-di-endo carboxylic acid imide used therein of an equimolar amount of 5-endo-hydroxy-N-(2-dimethylaminoethyl)-bicyclo-[2.2.1]heptane-2,3-di-endo-carboxylic acid imide produces the title product.

In a like manner, the procedures of Examples 1–3 and 5–8 may be repeated using 5-endo-hydroxy-N-(2-dimethylaminoethyl)-bicyclo[2.2.1]heptane-2,3-di-endo carboxylic acid imide as the alcohol starting material to produce the appropriate 5-endo-(heterocyclic-carbonyloxy)-N-(2-dimethylaminoethyl)-bicyclo[2.2.1]hetpane-2,3-di-endo carboxylic acid imide hydrochlorides.

EXAMPLE 10

5-endo-(2-Chloroquinoline-4-carbonyloxy)-N-(3-piperidinopropyl)-bicyclo[2.2.1]heptane-2,3-di-endo carboxylic acid imide hydrochloride (Compound of formula I where R=2-chloroquinoline-4-carbonyl, n=3, $R^4$ and

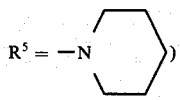

Substitution in the procedure of Example 4 for the 5-endo-hydroxy-N-(3-dimethylaminopropyl)-bicyclo[2.2.1]-heptane-2,3-di-endo carboxylic acid imide used therein of an equimolar amount of 5-endo-hydroxy-N-(3-piperidinopropyl)-bicyclo[2.2.1]heptane-2,3-di-endo carboxylic acid imide produces the title product.

In a like manner, the procedures of Examples 1–3 and 5–8 may be repeated using 5-endo-hydroxy-N-(3-piperidinopropyl)-bicyclo[2.2.1]heptane-2,3-di-endo carboxylic acid as the alcohol starting material to produce the appropriate 5-endo-(heterocyclic-carbonyloxy)-N-(3-piperidinopropyl)-bicyclo[2.2.1]heptane-2,3-di-endo carboxylic acid imide hydrochlorides.

EXAMPLE 11

5-endo-(2-Chloroquinoline-4-carbonyloxy)-N-(2-morpholinoethyl)-bicyclo[2.2.1]heptane-2,3-di-endo carboxylic acid imide hydrochloride (Compound of formula I where R=2-chloroquinoline-4-carbonyl, n=2, $R^4$ and

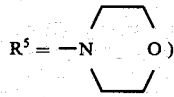

Substitution in the procedure of Example 4 for the 5-endo-hydroxy-N-(3-dimethylaminopropyl)-bicyclo[2.2.1]heptane-2,3di-endo carboxylic acid imide used therein of an equimolar amount of 5-endo-hydroxy-N-(2-morpholinoethyl)-bicyclo[2.2.1]-heptane-2,3-di-endo carboxylic acid imide produces the title product.

In a like manner, the procedures of Examples 1–3 and 5–8 may be repeated using 5-endo-hydroxy-N-(2-morpholinoethyl)-bicyclo[2.2.1]heptane-2,3-di-endo carboxylic acid as the alcohol starting material to produce the appropriate 5-endo-(heterocyclic-carbonyloxy)-N-(2-morpholinoethyl)-bicyclo[2.2.1]heptane-2,3-di-endo carboxylic acid imide hydrochlorides.

EXAMPLE 12

5-endo-(2-Chloroquinoline-4-carbonyloxy)-N-(3-morpholinopropyl)-bicyclo[2.2.1]heptane-2,3-di-endo carboxylic acid imide hydrochloride (Compound of formula I where R=2-chloroquinoline-4-carbonyl, n=3, $R^4$ and

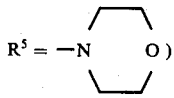

Substitution in the procedure of Example 4 for the 5-endo-hydroxy-N-(3-dimethylaminopropyl)-bicyclo[2.2.1]heptane-2,3-di-endo carboxylic acid imide used therein of an equimolar amount of 5-endo-hydroxy-N-(3-morpholinopropyl)-bicyclo[2.2.1]-heptane-2,3-di-endo carboxylic acid imide produces the title product.

In a like manner, the procedures of Examples 1–3 and 5–8 may be repeated using 5-endo-hydroxy-N-(3-morpholinopropyl)-bicyclo[2.2.1]heptane-2,3-di-endo carboxylic acid as the alcohol starting material to produce the appropriate 5-endo-(heterocyclic-carbonyloxy)-N-(3-morpholinopropyl)-bicyclo[2.2.1]heptane-2,3-di-endo carboxylic acid imide hydrochlorides.

EXAMPLE 13

5-endo-(2-Quinaldoyloxy)-N-(3-aminopropyl)-bicyclo[2.2.1]-heptane-2,3-di-endo carboxylic acid imide (Compound of formula I where R=2-quinaldoyloxy, n=3, $R^4$ and $R^5$=H)

Substitution in the procedure of Example 1 for the 5-endo-hydroxy-N-(3-dimethylaminopropyl)-bicyclo[2.2.1]heptane-2,3-di-endo carboxylic acid imide used therein of an equimolar amount of 5-endo-hydroxy-N-(2-cyanoethyl)-bicyclo[2.2.1]heptane-2,3-di-endo carboxylic acid imide produces the intermediate 5-endo-(2-quinaldoyloxy)-N-(2-cyanoethyl)-bicyclo[2.2.1]heptane-2,3-di-endo carboxylic acid imide. One-tenth mole of the above intermediate is dissolved in 200 ml. of ethanol and hydrogenated at 60 p.s.i. using Pd/C and hydrogen until 0.2 mole of hydrogen is absorbed to produce the title product.

In a like manner, the procedures of Examples 2-3, and 6-8 (with the proviso that acids of Example 8 containing hydroxy-substituents cannot be used) may be repeated using 5-endo-hydroxy-N-(2-cyanoethyl)-bicyclo[2.2.1]heptane-2,3-di-endo carboxylic acid as the alcohol starting material to produce the appropriate 5-endo-(heterocyclic-carbonyloxy)-N-(2-cyanoethyl)-bicyclo[2.2.1]heptane-2,3-di-endo carboxylic acid imide intermediates which may be hydrogenated as described above to give the desired 5-endo-(heterocyclic-carbonyloxy)-N-(3-aminopropyl)-bicyclo[2.2.1]heptane-2,3-di-endo carboxylic acid imides.

EXAMPLE 14

5-endo-(2-Chloroquinoline-4-carbonyloxy)-N-(2-diethylaminoethyl)-bicyclo[2.2.1]heptane-2,3-di-endo carboxylic acid imide hydrochloride (Compound of formula I where R=2-chloroquinoline-4-carbonyloxy, n=2, $R^4$ and $R^5$=$C_2H_5$)

Substitution in the procedure of Example 4 for the 5-endo-hydroxy-N-(3-dimethylaminopropyl)-bicyclo[2.2.1]heptane-2,3-di-endo carboxylic acid imide used therein of an equimolar amount of 5-endo-hydroxy-N-(2-diethylaminoethyl)-bicyclo[2.2.1]-heptane-2,3-di-endo carboxylic acid imide produces the title product.

In a like manner, the procedures of Examples 1-3 and 5-8 may be repeated using 5-endo-hydroxy-N-(diethylaminoethyl)bicyclo[2.2.1]heptane-2,3-di-endo carboxylic acid imide as the alcohol starting material to produce the appropriate 5-endo(heterocycliccarbonyloxy)-N-(2-diethylaminoethyl)-bicyclo[2.2.1]heptane-2,3-di-endo carboxylic acid imide hydrochlorides.

EXAMPLE 15

5-endo-(2-Chloroquinoline-4-carbonyloxy)-N-(4-dimethylaminobutyl)-bicyclo[2.2.1]heptane-2,3-di-endo carboxylic acid imide hydrochloride (Compound of formula I where R=2-chloroquinoline-4-carbonyl, n=4, $R^4$ and $R^5$=$CH_3$)

Substitution in the procedure of Example 4 for the 5-endo-hydroxy-N-(3-dimethylaminopropyl)-bicyclo[2.2.1]heptane-2,3-di-endo carboxylic acid imide used therein of an equimolar amount of 5-endo-hydroxy-N-(4-dimethylaminobutyl)-bicyclo[2.2.1]heptane-2,3-di-endo carboxylic acid imide produces the title product.

In a like manner, the procedures of Examples 1-3 and 5-8 may be repeated using 5-endo-hydroxy-N-(4-dimethylaminobutyl)-bicyclo[2.2.1]heptane-2,3-di-endo carboxylic acid imide as the alcohol starting material to produce the appropriate 5-endo-(heterocyclic-carbonyloxy)-N-(4-dimethylaminobutyl)-bicyclo[2.2.1]-heptane-2,3-di-endo carboxylic acid imide hydrochlorides.

EXAMPLE 16

5-endo-(2-Chloroquinoline-4-carbonyloxy)-N-(3-methylaminopropyl)-bicyclo[2.2.1]heptane-2,3-di-endo carboxylic acid imide hydrochloride (Compound of formula I where R=2-chloroquinoline-4-carbonyl, n=3, $R^4$=H, $R^5$=$CH_3$)

(A) 5-endo-(2-Chloroquinoline-4-carbonyloxy)-N-[3-(2,2,2-trichloroethoxycarbonyl)-3-methylaminopropyl]-bicyclo[2.2.1]heptane-2,3-di-endo carboxylic acid imide To a solution of 5-endo-(2-chloroquinoline-4-carbonyloxy)-N-(3-dimethylaminopropyl)-bicyclo[2.2.1]-heptane-2,3-di-endo carboxylic acid imide hydrochloride (21.5 mmoles) in 100 ml. of dry pyridine is added, portionwise and with stirring over 15 minutes, trichloroethyl chloroformate (21.5 mmoles). Stirring at 20° is continued for 20 minutes, followed by heating at 60°-65° in an oil bath for 75 minutes. The solution is then cooled and stripped of solvent under reduced pressure at 45°. The residue is dissolved in $CH_2Cl_2$ and washed successively with $H_2O$, cold dilute HCl, $H_2O$, 5% $Na_2CO_3$ solution and brine. Drying ($MgSO_4$) and solvent removal give a mixture of 5-endo-(2-chloroquinoline-4-carbonyloxy)-N-(3-dimethylaminopropyl)-bicyclo[2.2.1]heptane-2,3-di-endo carboxylic acid imide and 5-endo-(2-chloroquinoline-4-carbonyloxy)-N-(3-(2,2,2-trichloroethoxycarbonyl)3-methylaminopropyl)-bicyclo[2.2.1]heptane-2,3-di-endo carboxylic acid imide. Trituration with diethyl ether gives a solid which is then recrystallized from ethyl acetate-diethyl ether to give essentially pure title product.

(B) 5-endo-(2-Chloroquinoline-4-carbonyloxy)-N-(3-methylaminopropyl)-bicyclo[2.2.1]heptane-2,3-di-endo-carboxylic acid imide hydrochloride The product of part (A) (2.61 mmoles) is suspended in 90% acetic acid (100 ml.) and 7 g. of zinc dust is added portionwise with stirring over one minute. After stirring at 20° for 21 hours, the excess zinc and salts are removed by filtration and the cake is washed with 30 ml. of 90% acetic acid. The filtrate is stripped at 40° and the remaining gum is treated with saturated $NaHCO_3$ solution and then 1 N NaOH solution until it is distinctly basic. Extraction with ethyl acetate is followed by washing with $H_2O$ and brine. Drying ($MgSO_4$) and stripping gives a solid which is dissolved in 2:1 absolute ethanol/diethyl ether and treated with HCl gas. Solvent removal and trituration with hot 3:1 ethyl acetate/absolute ethanol gives the crude title product. Boiling in 3:1 acetonitrile/absolute ethanol and dilution with diethyl ether gives the pure title product.

In a like manner, the procedure of Example 16 may be repeated using the title products of Examples 1-3 and 5-8 to give the appropriate 5-endo-(heterocycliccarbonyloxy)-N-(3-methylaminopropyl)-bicyclo[2.2.1-

]heptane-2,3-di-endo carboxylic acid imide hydrochlorides.

EXAMPLE 17

5-endo-(2-Chloroquinoline-4-carbonyloxy)-N-(3-isopropylaminopropyl)-bicyclo[2.2.1]heptane-2,3-di-endo carboxylic acid imide hydrochloride (Compound of formula I where R=2-chloroquinoline-4-carbonyl, n=3, $R^4$=i-propyl, $R^5$=H)

The chloro acid chloride prepared in Example 4 (1.75 moles) and 5-endo-hydroxy-N-(N'-benzyloxycarbonyl-3-isopropylaminopropyl)-bicyclo[2.2.1]heptane-2,3-di-endo carboxylic acid imide (1.14 mmoles) are heated in dry tetrachloroethane (75 ml.) at 120° for 2.75 hours. The solvent is removed under reduced pressure and the residual oil is partitioned between ethyl acetate and water. After separation of the layers, the aqueous layer is extracted with a second portion of ethyl acetate. The combined organic extracts are washed with water and brine, dried and stripped of solvent to give a crude solid which can be recrystallized to give 5-endo-(2-chloroquinoline-4-carbonyloxy)-N-(N'-benzyloxycarbonyl-3-isopropylaminopropyl)-bicyclo[2.2.1]-heptane-2,3-di-endo carboxylic acid imide. Hydrogenolysis of this intermediate by the method disclosed in Example 23C. of Belgian Pat. No. 833,385 gives the title product.

In a like manner, the procedure of Example 17 may be repeated using the starting material acid halides or imidazolides of Examples 1–3 and 5–8 to give the appropriate 5-endo-(heterocyclic-carbonyloxy)-N-(3-isopropylaminopropyl)-bicyclo[2.2.1]-heptane-2,3-di-endo carboxylic acid imide hydrochlorides.

EXAMPLE 18

General Method for the Resolution of the racemic 5-endo-(heterocyclic-carbonyloxy)-N-[amino(lower)alkyl]-bicyclo-[2.2.1]heptane-2,3-di-endo carboxylic acid imides into their (+) and (−) enantiomers.

1. Treatment of the racemic base (prepared, e.g. by neutralization of the hydrochloride salt with $Na_2CO_3$) with (+)-10 camphor-sulfonic acid in ethanol-water gives the diastereoisomeric salt of the (−)-isomer. Decomposition of this salt with aqueous sodium carbonate produces the (−)-enantiomer which may be converted to the hydrochloride salt with ethanolic hydrogen chloride.

2. The mother liquor from step (1) is concentrated to leave a mixture of the diastereoisomeric salts. Neutralization of this mixture with aqueous sodium carbonate gives a mixture of the (+)-and (−)-isomers, which was greatly enriched in the (+)-enantiomer. The mixture is purified through diastereoisomer formation with (−)-tartaric acid to give the salt of (−)-tartaric acid with the (+)-enantiomer which is subsequently decomposed to produce the (+)-enantiomer.

EXAMPLE 19

(+)-5-endo-(2-Chloroquinoline-4-carbonyloxy)-N-(3-dimethylaminopropyl)-bicyclo[2.2.1]heptane-2,3-di-endo carboxylic acid imide hydrochloride Substitution in the procedure of Example 4 for the (±)-5-endo-hydroxy-N-(3-dimethylaminopropyl)-bicyclo[2.2.1]-heptane-2,3-di-endo carboxylic acid imide used therein of an equimolar amount of (+)-5-endo-hydroxy-N-(3-dimethylaminopropyl)-bicyclo[2.2.1-]heptane-2,3-di-endo carboxylic acid imide (prepared according to Ex. 19A of Belgian Pat. No. 833,385) gives the title product.

In a like manner, the procedures of Examples 1–3 and 5–17 may be repeated using the (+)-enantiomer of the appropriate alcohol as the starting material to give the essentially pure dextrorotatory isomers of the 5-endo-(heterocyclic-carbonyloxy)-N-[amino(lower)alkyl]-bicyclo[2.2.1]heptane-2,3-di-endo carboxylic acid imide hydrochloride (or free base) products.

EXAMPLE 20

(−)-5-endo-(2-Chloroquinoline-4-carbonyloxy)-N-(3-dimethylaminopropyl)-bicyclo[2.2.1]heptane-2,3-di-endo carboxylic acid imide hydrochloride Substitution in the procedure of Example 4 for the (±)-5-endo-hydroxy-N-(3-dimethylaminopropyl)-bicyclo[2.2.1]heptane-2,3-di-endocarboxylic acid imide used therein of an equimolar amount of (−)-5-endo-hydroxy-N-(3-dimethylaminopropyl)-bicyclo[2.2.1]heptane-2,3-di-endo carboxylic acid imide (prepared according to Ex. 20A of Belgian Pat. No. 833,385) produces the title product.

In a like manner, the procedures of Examples 1–3 and 5–17 may be repeated using the (−)-enantiomer of the appropriate alcohol as the starting material to give the essentially pure levorotatory isomers of the 5-endo-(heterocyclic-carbonyloxy)-N-[amino(lower)alkyl]-bicyclo[2.2.1]-heptane-2,3-di-endo carboxylic acid imide hydrochloride (or free base) products.

We claim:

1. A compound having the formula

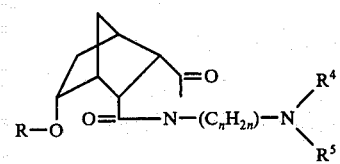

I wherein R is a group of the formula

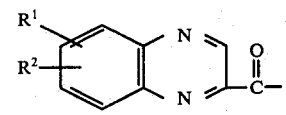

in which $R^1$ and $R^2$ are alike or different and are each hydrogen, chloro, bromo, fluoro, (lower)alkyl, nitro, trifluoromethyl, hydroxy or (lower)alkoxy, n is an integer of 2 to 4 inclusive and $R^4$ and $R^5$ are alike or different and each is hydrogen, (lower)alkyl or, when taken together with the nitrogen, a heterocyclic ring of the formula

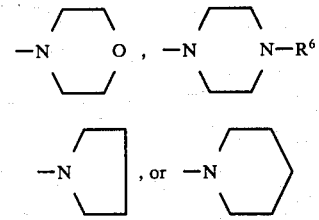

in which $R^6$ is (lower)alkyl; or a pharmaceutically acceptable acid addition salt thereof.

2. The essentially pure dextrorotatory isomer of a compound of claim 1.

3. The essentially pure levorotatory isomer of a compounds of claim 1.

4. A compound having the formula

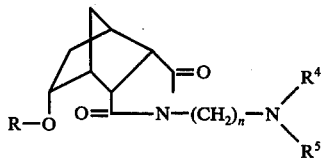

wherein R is a group of the formula

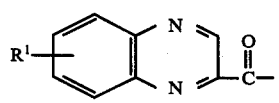

in which $R^1$ is hydrogen, chloro, bromo, fluoro, (lower)alkyl, nitro, trifluoromethyl, hydroxy or (lower)alkoxy, n is an integer of 2 to 4 inclusive and $R^4$ and $R^5$ are alike or different and are each hydrogen, (lower)alkyl or, when taken together with the nitrogen, a heterocyclic ring of the formula

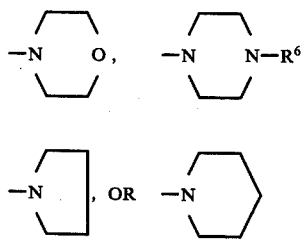

in which $R^6$ is (lower)alkyl; or a pharmaceutically acceptable acid addition salt thereof.

5. The essentially pure levorotatory isomer of a compound of claim 4.

6. The essentially pure dextrorotatory isomers of a compound of claim 4.

7. A compound of claim 4 wherein $R^4$ and $R^5$ are alike or different and each is hydrogen or (lower)alkyl; or a pharmaceutically acceptable acid addition salt thereof.

8. A compound of claim 4 wherein n is 3 and $R^4$ and $R^5$ are each methyl; or a pharmaceutically acceptable acid addition salt thereof.

9. A compound having the formula

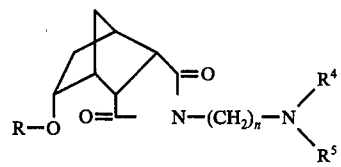

wherein R is a group of the formula

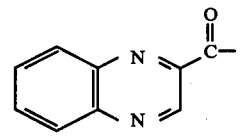

n is an integer of 2 to 4 inclusive and $R^4$ and $R^5$ are alike or different and are each hydrogen, (lower)alkyl or, when taken together with the nitrogen, a heterocyclic ring of the formula

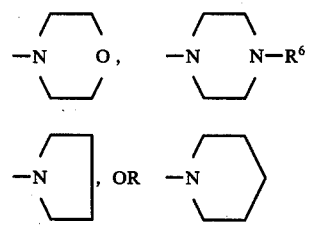

in which $R^6$ is (lower)alkyl; or a pharmaceutically acceptable acid addition salt thereof.

10. The essentially pure levorotatory isomer of a compound of claim 9.

11. The essentially pure dextrorotatory isomer of a compounds of claim 9.

12. A compound of claim 9 wherein $R^4$ and $R^5$ are alike or different and each is hydrogen or (lower)alkyl; or a pharmaceutically acceptable acid addition salt thereof.

13. A compound of claim 9 wherein n is 3 and $R^4$ and $R^5$ are each methyl; or a pharmaceutically acceptable acid addition salt thereof.

14. The compound having the formula

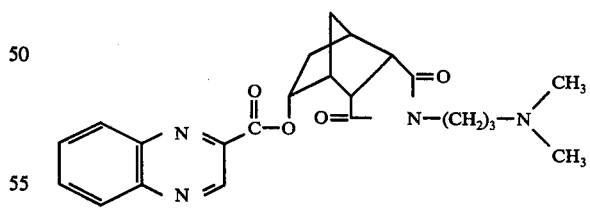

or the hydrochloride salt thereof.

15. The essentially pure levorotatory isomer of a compound of claim 14.

16. The essentially pure dextrorotatory isomer of a compound of claim 14.